United States Patent [19]

Eakin

[11] Patent Number: 4,875,898
[45] Date of Patent: Oct. 24, 1989

[54] INCONTINENCE DEVICE FOR WOMEN

[76] Inventor: Thomas G. Eakin, 965 Upper Newtownards Rd., Dundonald, Belfast BT16 ORL, Northern Ireland

[21] Appl. No.: 307,235

[22] Filed: Feb. 6, 1989

Related U.S. Application Data

[63] Continuation of Ser. 65,162, Jun. 19, 1987, abandoned, which is a continuation of Ser. No. 741,667, filed as PCT GB84/00331 on Sep. 27, 1984, published as WO85/01438 on Apr. 11, 1985, abandoned.

[30] Foreign Application Priority Data

Sep. 27, 1983 [GB] United Kingdom ............... 8325848
Sep. 27, 1983 [GB] United Kingdom ............... 8325847
Sep. 18, 1984 [GB] United Kingdom ............... 8423591

[51] Int. Cl.$^4$ ................................................ A61F 5/44
[52] U.S. Cl. ............................ 604/331; 128/DIG. 25
[58] Field of Search ................. 128/DIG. 25, 325; 604/328, 329, 330, 331; 4/144.4, 144.3, 144.2, 144.1

[56] References Cited

U.S. PATENT DOCUMENTS

| | | |
|---|---|---|
| 2,638,093 | 5/1953 | Kulick . |
| 3,116,734 | 1/1964 | Terman . |
| 3,528,423 | 9/1970 | Lee ................................ 604/329 |
| 3,661,155 | 5/1972 | Lindan ........................... 604/329 |
| 3,705,575 | 12/1972 | Edwards ................... 128/DIG. 25 |
| 4,194,508 | 3/1980 | Anderson ......................... 4/144.3 |
| 4,246,901 | 1/1981 | Frosch ............................ 604/329 |
| 4,270,539 | 6/1981 | Frosch ........................... 4/144.3 |
| 4,496,355 | 1/1985 | Hall et al. ...................... 4/144.3 |

FOREIGN PATENT DOCUMENTS

| | | |
|---|---|---|
| 867348 | 5/1961 | United Kingdom . |
| 1115727 | 5/1968 | United Kingdom . |
| 1193261 | 5/1970 | United Kingdom . |
| 1216662 | 12/1970 | United Kingdom . |
| 1253497 | 11/1971 | United Kingdom . |
| 1289107 | 9/1972 | United Kingdom . |
| 1315964 | 5/1973 | United Kingdom . |
| 1359343 | 7/1974 | United Kingdom . |
| 2090144 | 7/1982 | United Kingdom ............... 604/331 |

OTHER PUBLICATIONS

"Vertical Median Section of Female Pelvis", FIG. 570, p. 1026, Anatomy, Gray, FRS, Bounty Books, New York, 1977.

Primary Examiner—Jerome L. Kruter
Attorney, Agent, or Firm—Millen, White & Zelano

[57] ABSTRACT

An incontinence device for use by females wherein the device includes a forwardly facing internal leg, the internal leg having a curved surface dimensioned so as to conform to the anterior vaginal wall. The device further includes an external leg connected to the internal leg by a U-shaped bite portion to define therewith a generally J-shaped structure. The external leg is dimensioned so as to conform to the mons veneris of the female using the device. The device includes a further internal leg extending rearwardly therefrom toward the cervix.

10 Claims, 4 Drawing Sheets

INCONTINENCE DEVICE FOR WOMEN

This application is a continuation, of application Ser. No. 065,162, filed June 19, 1987, which is a cont. of Ser. No. 741,667, filed as PCT GB84/00331 on Sep. 27, 1984, published as WO85/01438 on Apr. 11, 1985, now abandoned.

BACKGROUND OF THE INVENTION

(1) Field of the Invention

The present invention relates to an incontinence device particularly adapted for the use of female patients.

(2) Technical Considerations and Prior Art

The problem of incontinence in women has long been difficult to solve. In hospitals the use of a self-retaining catheter inserted into the urethra is normal practice, and while this successfully controls involuntary flow, it brings with it the problem of infection. In addition, professional help is normally required in replacing the catheter, which makes it inconvenient for use when the patient is not in the hospital. The use of known incontinence clothing has little more than an external cosmetic effect, and since urine flow is not prevented, the patient remains continually wet and uncomfortable.

Incontinence in females may be a transient condition or a long-term condition or an involuntary condition.

SUMMARY OF THE INVENTION

The present invention in its various aspects consists essentially of a simple molded device which can be worn in the vagina, and which is easy to use in that it can easily be inserted and removed by the patient herself and worn, when required, at home. It may conveniently be molded in a one-piece form which is cheap to manufacture and easy to clean or cheap enough to be disposable.

The condition referred to above as transient may be when the incontinence has been caused by trauma, such as an operation, and the patient can be expected gradually to regain control of bladder function. Here a drainage version of the device in accordance with the invention may be most appropriate, since it will accommodate inadvertent bladder leakage but enable the user to observe her increasing degree of control and gain confidence therefrom.

This form of device is also useful where the patient has long-term incontinence and, for example, is bedridden.

The condition referred to as long-term may, on the other hand, require more complete control as indeed may the transient condition when the patient has left the hospital. Here a restrictive version of the invention is used in which the internal portion of the device occludes the urethra so that the device is removed to discharge the bladder.

The condition referred to above as involuntary is a further condition of female incontinence which is known as stress incontinence. This is a condition in which involuntary discharge of urine occurs only in certain circumstances, such as when the person coughs or jumps. This is caused by the bladder dropping. Known techniques which have been applied to try to control this condition comprise the so-called watch spring pessary and a surgical procedure in which a ligature is placed around the urethra. Both techniques aim to relocate the urethra in the normal position. The former technique is not very effective, the device tending to slip from the correct position, and the latter technique involves a surgical procedure.

An incontinence device in accordance with the present invention may consist of two limbs which together form a generally U- or V-shaped configuration, a first or upper limb affording the internal portion of the device and a second or lower limb affording the external portion of the device and to which is attached the tensioning means.

The first limb may be shorter than the second limb, or they may be of essentially equal length, but this is not essential. The upper limb may be significantly shorter provided the necessary seal can be maintained. On the other hand, an arrangement in which the lower or outer limb is shorter is not excluded.

In those forms of the incontinence device which are provided with occlusion means, these may be provided on the upper limb by a forwardly facing protuberance, the pressure of which on the vaginal wall causes or assists the urethral occlusion.

The device is held in position by a rearwardly-extending portion which is pressed against the dorsal vaginal wall.

This rearwardly-extending portion may be either a rigid loop attached to the upper limb, or a molded extension to the base of the U, or preferably may be generally shaped so as to conform to the lower vaginal wall proximate to the vaginal opening.

In another form of the invention, a rearwardly-extending portion extends from the region of the upper end of the interior portion and across the vagina laterally and extends into the region of the cervix or past it but stops short of the dorsal wall of the vagina. This assists in maintaining the device in the laterally correct position and is particularly useful in the stress incontinence version of the invention.

The device is made of a rigid or semi-rigid substance and is preferably provided with soft pads or coverings for comfort.

The tensioning means may conveniently comprise a strap or cord attached at one end to a belt, the tension being due to the elasticity of the cord or that of the belt, or both, the belt also constituting the securing means.

It may be desirable, for comfort, for the strap to be of a soft or padded material or for it to be sheathed.

In another form of the invention, the device is generally rigid but is provided with a flexible portion between the limbs allowing hinging motion therebetween.

In order to produce or assist in producing a fluidtight seal between the anterior vaginal wall and the inner face of the first limb, a suitable substance of putty-like consistency may be used.

The invention may be put into practice in various ways, and a number of specific embodiments will be described by way of example with reference to the accompanying drawings, in which:

Figure 3A:
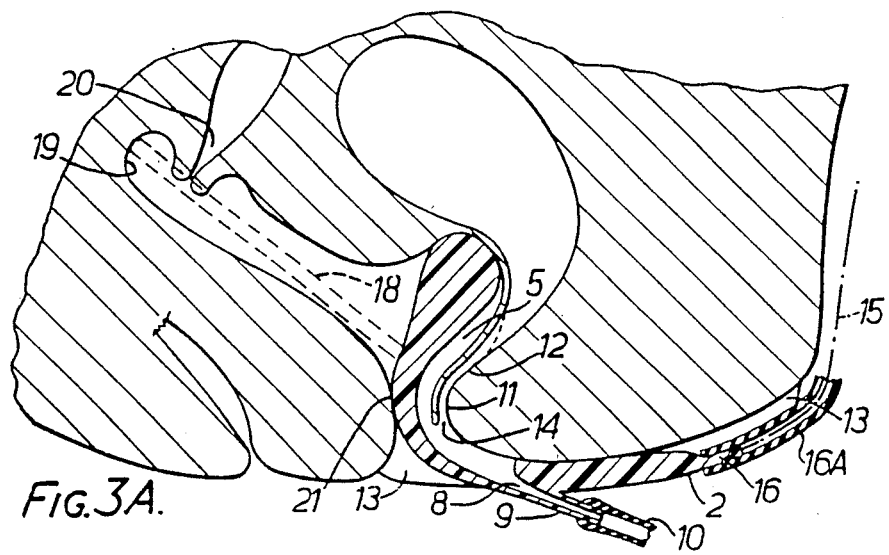
FIG. 3A is a medial cross section of the lower part of the female body, showing the embodiment of FIG. 1 in position, in which position it is held either by an external strap (chained line) or by the external strap and an internal loop (dashed line)
Figure 3B:
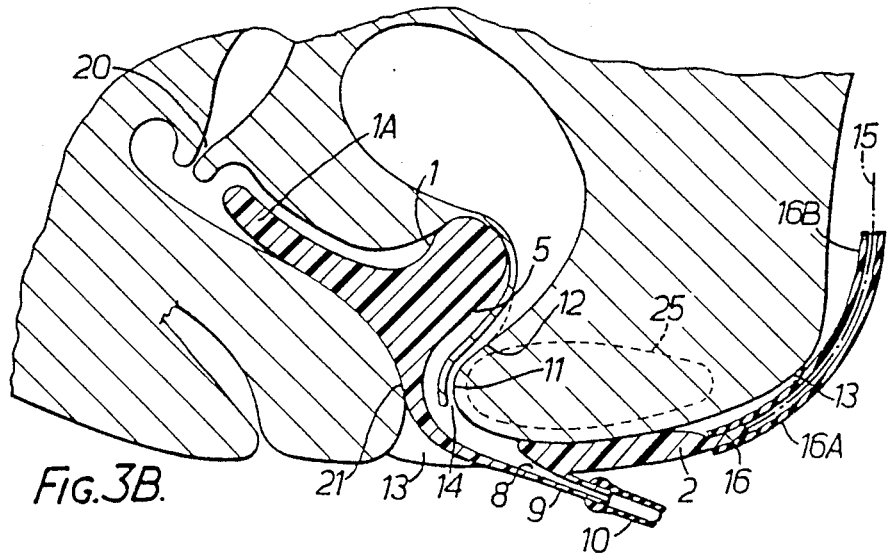
FIG. 3B is a view similar to FIG. 3A showing a first modification of the first embodiment, provided with sheathing of the strap and a modified internal positioning arrangement.
Figure 8:
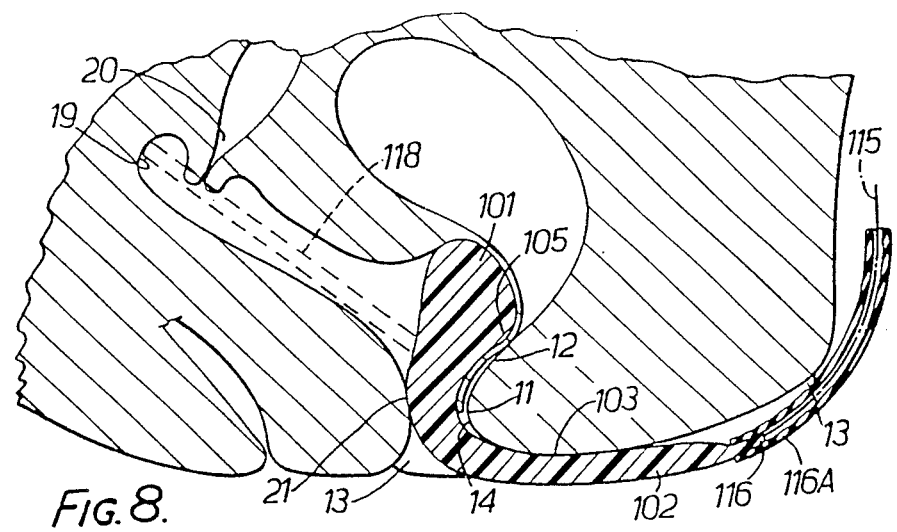
Figure 9:
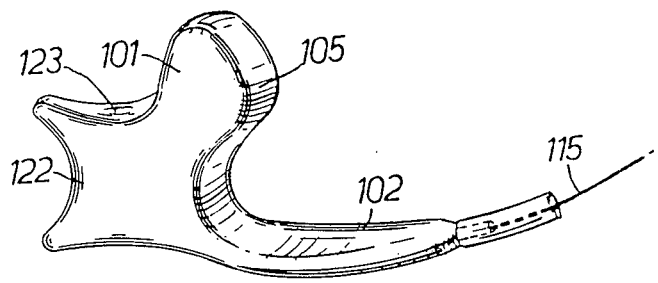
Figure 10:
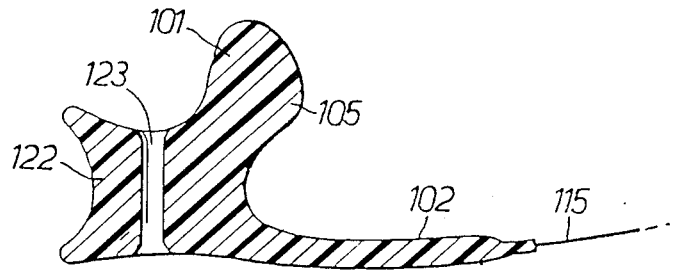

The differences between FIGS. 3A, 3B and 8 reflect the wide range of different shapes and sizes of the vaginal cavity, which in fact really only exists as a cavity when a member is inserted into it. The most constant feature is the location of the anterior dorsal vaginal wall and its relationship to the pubic bone (25 in FIG. 3B). However, even the shape of the pubic bone can vary widely.

DESCRIPTION OF THE PREFERRED EMBODIMENT

Figure 1A:
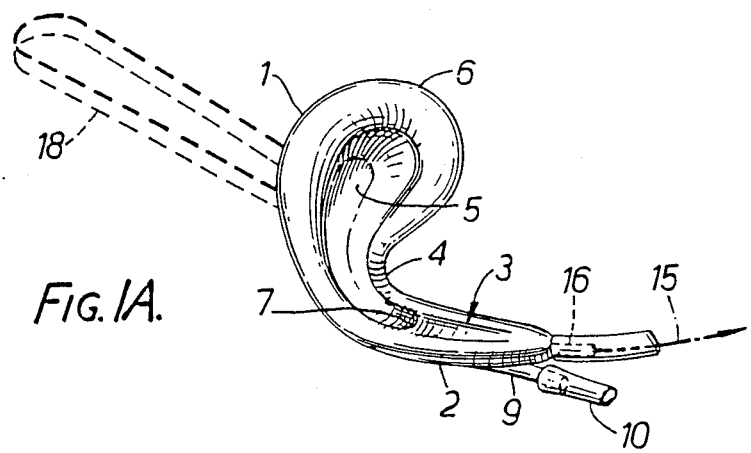
FIG. 1A is a perspective view of a first embodiment of the invention showing a drainage version of the invention.
Figure 1B:
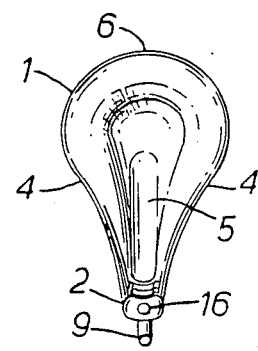
FIG. 1B is a front elevation of the device shown in FIG. 1A.
Figure 2:
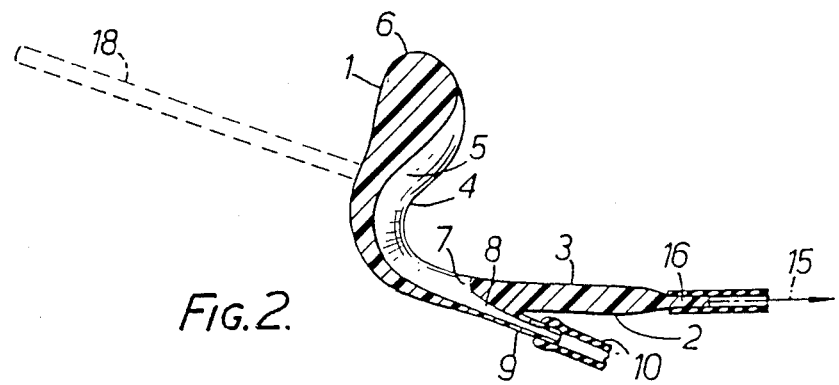
FIG. 2 is a medial cross section of the embodiment of FIGS. 1A and 1B illustrating the drainage channel and tube outlet.

In the first embodiment, the invention takes the form shown in FIG. 1 and consists of two integrally-connected limbs 1 and 2, the inner or upper limb 1 broadening out into a tongue or, in elevation (see FIG. 1B), light-bulb-shaped plan, and the outer of limb 2 being narrower and not broadening out at its end. The limbs 1 and 2 together provide a generally U- or V-shaped configuration, the inner face 3 of the lower limb of the U being generally flat or concave. The inner face 4 of the upper limb 1 affords a centrally disposed, medially extending duct, channel or groove 5 defined by the edges of the limb 1, which edges are slightly rounded at its far end 6.

The limbs 1 and 2 form internal and external legs respectively with the external leg (limb 2) being connected to the internal leg (limb 1) by a U-shaped portion (generally at inner face 4) so that the external leg forms with the internal leg a generally J-shaped structure. As can be seen from FIGS. 3A and 3B, the external leg (limb 2) is dimensioned to conform to the mons veneris of the female using the device.

The edges 4 of the channel 5 may also be rounded along its length. The channel issues out of the end 6 of the limb 1 and extends around the base of the U some distance (e.g., about 20 to 30%, e.g., 25% of the length) along the lower limb 2, where it terminates on the surface of the limb 2 in a rounded end 7. The channel 5 communicates with an internal duct 8, at or near its end 7, which duct extends more or less diagonally through the limb 2 to emerge through its outer face at 9, at or near the end of the limb 2. This angle enables the bladder to be emptied even when the woman is sitting down. The duct 8 is thereconnected to, or continues as a tube 10. In use, the limb 1 of the device is inserted into the entrance of the vagina and is positioned so as to be located in the vagina as shown in FIG. 3A, with the limb 1 being placed against the anterior vaginal wall 11, the channel 5 being positioned so as to follow the course of the urethra 12. It is not essential for the limb 1 to extend as far into the vagina as shown in FIG. 3A. It may be shorter, provided an adequate seal can be maintained between the vaginal wall 11 and the edges 4 of the channel 5. The lower limb 2 points forwardly and is positioned against the outer surface of the body, within the vulva 13. The urethral opening 14 is thus positioned within the channel 5. Any urine escaping from the urethral opening 14 will pass along the channel 5, through the duct 8, and pass into the tube 10 where it may be collected by any suitable means, such as a receptacle attached to the patient's leg.

Figure 4:
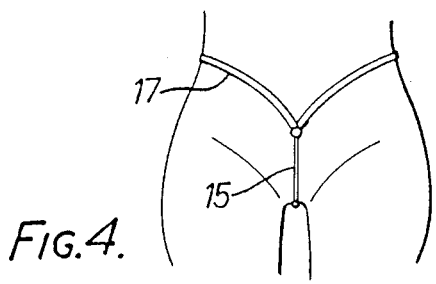
FIG. 4 illustrates one method of securing the embodiments of the invention in position, in which an extensible strap and belt are used.

The device is held in position by means of external tensioning means, one form of which is a strap 15 which is attached to or is a continuation of the second limb 2 from its forward end 16. The strap 15 (which may be padded or sheathed for comfort) may conveniently be attached to a belt 17 as shown in FIG. 4 and is maintained in tension by its own elasticity or that of the belt 17, or both. When the strap 15 is sheathed, this is conveniently achieved by a plastics tube 16A which may extend (as shown in FIG. 3B) from the end of limb 2 (to which it may be connected) out beyond the vulva 13, e.g., as far as 16B (see FIG. 3B). This prevents the tensioning means from rubbing the user. The means 15 may only be elastic within such a tube and thereafter be connected to the belt by an inelastic connection. The belt may be elastic or inelastic. This tension causes the limb 1 to be pressed against the anterior vaginal wall 11. The necessary seal between the vaginal wall 11 and the edges 4 of the channel 5 may be enhanced by lining the edges 4 with any suitable material, such as a soft pad, or a cohesive gum of suitable consistency may be used. Suitable gums include a mixture of Karaya gum, glycerine and gelatine mixed to a putty-like consistency, or, alternatively, liquid polymers, such as cellulose-polybutene combination, may be used.

FIG. 3B shows a further modification in which a dorsal extension 1A of generally duck-billed shape extends rearwardly from the top back face of the limb 1 towards or past the cervix, but stops short of the dorsal wall of the vagina and extends across this region of the vagina. A dorsal extension of this sort is also shown and described in FIG. 11 (see reference 207). This extension helps maintain accurate lateral location of the device in use.

In a first modification of the device, the necessary support may be increased internally, particularly against lateral movement. This may take the form of a generally rigid but resilient loop 18, which is attached to the back or outer face of the limb 1, as shown in FIG. 1 and 3A by dashed lines. In this modification, the belt and strap again hold the device in place and cause the limb 1 to be pressed against the anterior vaginal wall 11 in the position previously described. The loop 18 being pressed against the upper dorsal vaginal wall 19 behind the cervix 20 with the natural elasticity of the vaginal wall 19 helps to hold the device in place, particularly against lateral movement.

In a third modification, the end of the channel 5 is left open, rather than communicating with the duct 8 and tube 10 (which are then no longer needed and can be omitted).

The device may be made of any suitably flexible material, such as rubber, or it may be made of a more rigid material, such as polypropylene, and provided with pads of compressible material for comfort in the necessary regions. The structure should be sufficiently rigid to ensure secure location in the vagina and to enable the force exerted by the strap 15 to pull the limb 1 against the vaginal wall 11. If the device is made of a generally rigid material, the base of the U, between the limbs 1 and 2, may be made of a more flexible material to allow some hinging movement between the limbs, thus accommodating personal differences in vaginal shape. When the loop 18 is present, the hinging embodiment can be used or the device can be made of more flexible material throughout. The use of a non-reactive material may be useful to patients with allergies to rubber of silicone products.

This first version, the drainage version, of the invention deals with incontinence by collecting the urine.

The second version, the restrictive version, of the invention mechanically causes retention of the urine.

Figure 5:
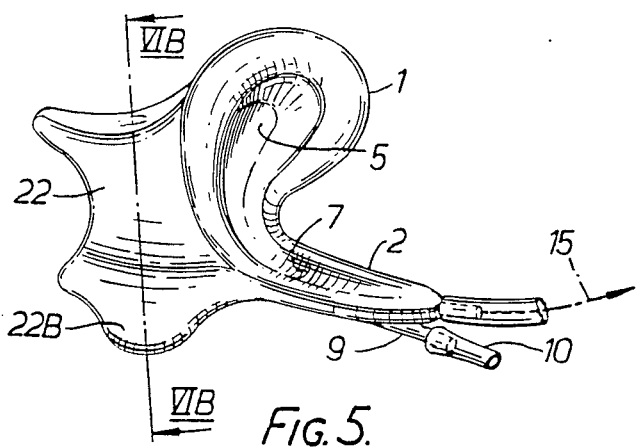
FIG. 5 is a perspective view of the second embodiment of the invention showing a restrictive version of the invention.
Figure 7:
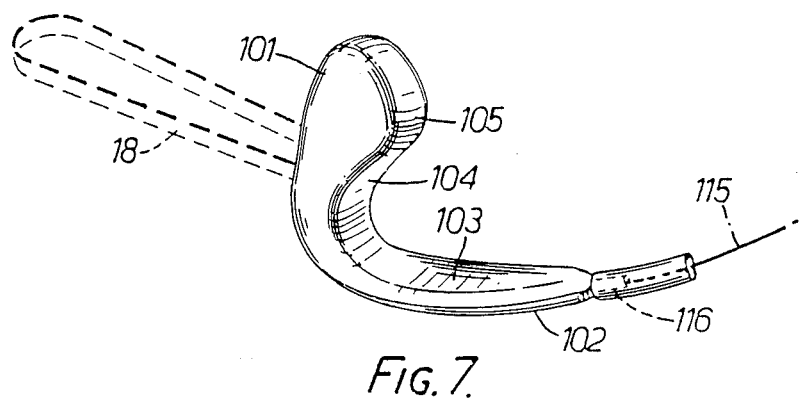

In the second embodiment, this restrictive version of the invention takes the form shown in FIG. 5 and consists of two integrally connected limbs 101,102. The limbs 101 and 102 together provide a generally U- or V-shaped configuration, the inner face 103 of the lower limb 102 being generally flat or concave. The inner face 104 of the upper limb is generally flat or convex and terminates in an inwardly-facing protuberance 105, of which the edges are rounded as shown in FIG. 7. In use, the limb 101 of the device is inserted into the entrance to the vagina and is positioned so as to be located in the vagina, as shown in FIG. 8, with the limb 101 positioning the inwardly facing protuberance 105 so as to be being placed against the anterior vaginal wall 11, following the line of the urethra 12.

The lower limb 102 points forwardly and is positioned against the outer surface of the body within the vulva 13. The device is held in position by means of tensioning means, one form of which is a strap 115 which is attached to or is a continuation of the lower limb 102 at its forward end 116. The strap 115 (which may be padded for comfort or sheathed, as described above in connection with FIG. 3B) may conveniently be attached to a belt 17 (as shown in FIG. 4 above) and is maintained in tension by its own elasticity or that of the belt 17, or both. This tension causes the limb 101 to be pressed against the anterior vaginal wall 11 directly over the course of the urethra 12. The pressure of the limb 101, and particularly that due to the protuberance 105, causes the urethra 12 to collapse (as shown in FIG. 8), so preventing urine flow.

Figure 6A:
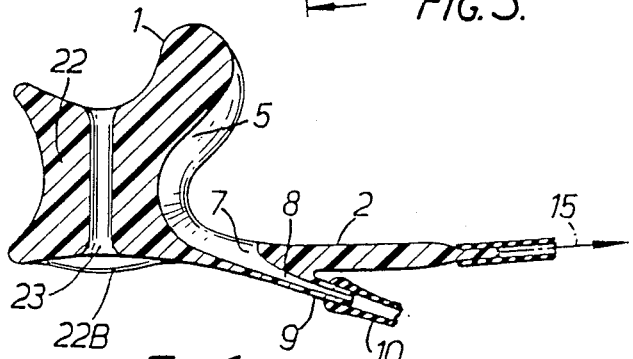
FIG. 6 is a medial cross section of the lower part of the female body showing the embodiment of FIG. 7 in position, in which position it is held either by an external strap (see FIG. 4) (chained line) or, in a first modification of this second embodiment, by the external strap and by an internal loop (dashed line)
Figure 6B:
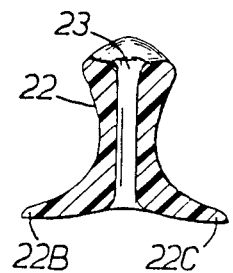

In a first modification of this second embodiment of the device, the necessary support may be increased internally particularly against lateral movement. This may take the form of a rigid loop 118 which is attached to the back or outer face of the limb 101, as shown in FIGS. 5 and 6 by dashed lines. In this modification, the belt and strap again hold the device in place, the limb 101 being pressed against the anterior vaginal wall 11 in the position previously described. The loop 118 being pressed against the upper dorsal vaginal wall 19 behind the cervix 20 with the natural elasticity of the vaginal wall 19 helps hold the device in place particularly against lateral movement.

It is not essential for the limb 101 to extend as far into the vagina as shown in FIG. 6. It may be shorter, provided that it extends far enough above the urethral opening 14 to allow the occlusion of the urethra 12 without significant leakage. The protuberance 105 at the end of the limb 101 is likewise not essential to the invention; the pressure of the limb 101 alone on the urethra 12 can be sufficient to cause it to collapse, but the protuberance aids certainty of operation.

The device may be made of any suitably flexible material, such as rubber, or it may be made of a more rigid material, such as polypropylene, and provided with pads of compressible material, for comfort, in the necessary regions. The structure should be sufficiently rigid to ensure secure location in the vagina and to enable the force exerted by the strap 15 to pull the limb 101 and the protuberance 105 against the interior vaginal wall 11 sufficiently hard to occlude the urethra 12. If the device is made of a generally rigid material, the base of the U, between the limbs 101 and 102, may be made of a more flexible material to allow some hinging movement between the limbs, thus accommodating personal differences in vaginal shape. When the loop 118 is present, the hinging embodiment may be used, or the device may be made of a more flexible material throughout.

Figure 11:
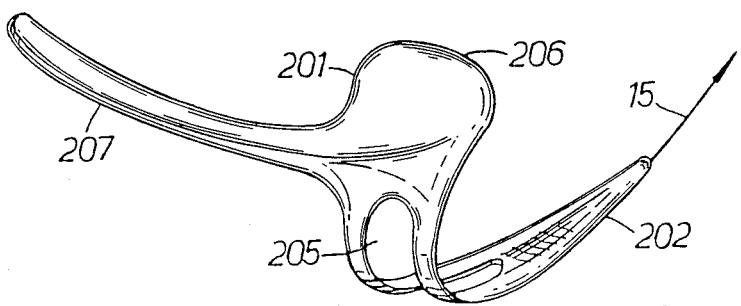

Referring now to FIG. 11, this shows the third embodiment of the invention, the stress incontinence version.

Here the inner limb 201 is generally of spoon shape, while the outer limb 202 is narrower. Again, the tensioning means extend away from the end of the limb 202 as in the other embodiments and as illustrated diagrammatically at 15. A slot-like duct 205 extends around the bend which joins the limbs 201 and 202, enabling urine to be discharged from the urethral opening 14 without the device needing to be removed from the vagina. The top edge 206 of the inner limb 201 holds the user's urethra in or near the normal position and reduces or alleviates stress incontinence.

I claim:
1. An incontinence device for use by females, the device comprising:
 a forward-extending, substantially rigid internal leg having a distal end, the internal leg having a forward-facing first curved surface so dimensioned as to conform to or contact the anterior vaginal wall of the female using the device and having a free end for positioning within the vagina;
 a U-shaped bight portion connected to the internal leg, the U-shaped bight portion having a curved surface being dimensioned to span the urethral orifice of the female using the device while being in close proximity therewith;
 an external leg connected at an acute angle with the internal leg by the U-shaped bight portion to define therewith a generally J-shaped structure with the external leg so dimensioned as to conform to the mons veneris of the female using the device; and
 a further, substantially rigid internal leg means connected to the device at the U-shaped bight portion and extending rearwardly from a surface thereof at a substantially fixed right angle to the forwardly extending internal leg and spaced from the distal end of the internal leg towards the cervix of the female using the device, the further leg assisting in retaining the device in position without the necessity of external securing means.

2. A device according to claim 1 in which said further internal leg extends across the vagina laterally and extends into the region of the cervix but stops short thereof.

3. A device according to claim 1 including a tether secured to the free end of the external leg for applying tension thereto, and means for maintaining tension on the tether when the device is in use.

4. A device according to claim 1 in which said internal leg is provided with occlusion means, said occlusion means being so dimensioned as to occlude the urethra of the female using the device.

5. A device according to claim 4 in which said occlusion means comprises a protuberance which presses against the urethra.

6. A device according to claim 1 in which said internal leg means has a medial channel therein arranged to follow the course of the urethra.

7. A device according to claim 6 including a duct communicating with the channel for channelling urine away from said device.

8. A device according to claim 7 in which said duct extends through said bight portion.

9. A device according to claim 8 including a tether secured to the free end of said external leg for applying tension thereto, and means for maintaining tension on said tether when said device is in use.

10. A device according to claim 9 in which said internal leg means, said further internal leg and said external leg are integral with each other.

* * * * *